(12) United States Patent
Krüger et al.

(10) Patent No.: US 10,821,247 B2
(45) Date of Patent: Nov. 3, 2020

(54) VENTILATOR AND OPERATING METHOD FOR A VENTILATOR WITH A DETERMINATION OF COUGH ATTACKS

(71) Applicant: Drägerwerk AG & Co. KGaA, Lübeck (DE)

(72) Inventors: Thomas Krüger, Reinfeld (DE); Henning Gerder, Lübeck (DE); Birger Landwehr, Lübeck (DE)

(73) Assignee: Drägerwerk AG & Co. KGaA, Lübeck (DE)

( * ) Notice: Subject to any disclaimer, the term of this patent is extended or adjusted under 35 U.S.C. 154(b) by 316 days.

(21) Appl. No.: 15/804,316

(22) Filed: Nov. 6, 2017

(65) Prior Publication Data

US 2018/0126104 A1    May 10, 2018

(30) Foreign Application Priority Data

Nov. 7, 2016    (DE) .................. 10 2016 013 140

(51) Int. Cl.
*A61M 16/00* (2006.01)
*A61B 5/08* (2006.01)
(Continued)

(52) U.S. Cl.
CPC ......... *A61M 16/024* (2017.08); *A61B 5/0823* (2013.01); *A61B 5/097* (2013.01); *A61B 5/4836* (2013.01); *A61M 16/0003* (2014.02); *A61M 16/0051* (2013.01); *A61M 16/026* (2017.08); *A61M 16/0875* (2013.01);
(Continued)

(58) Field of Classification Search
CPC .............. A61M 16/024; A61M 16/026; A61M 16/0875; A61M 16/0051; A61M 16/0003; A61M 2205/18; A61M 2016/0042; A61M 2016/0039; A61M 2016/0027; A61M 2016/0033; A61B 5/4836; A61B 5/097; A61B 5/0823
See application file for complete search history.

(56) References Cited

U.S. PATENT DOCUMENTS 2,904,035 A    9/1959  Andreasen
3,741,208 A *  6/1973  Jonsson ................ A61M 16/20
                                                        128/204.21
(Continued)

FOREIGN PATENT DOCUMENTS

WO    2007/085110 A1    8/2007

OTHER PUBLICATIONS

Breathing Cycle, Pathway Medicine, Apr. 11, 2012, webpage (http://www.pathwaymedicine.org/breathing-cycle).*
(Continued)

*Primary Examiner* — Michael J Tsai
(74) *Attorney, Agent, or Firm* — McGlew and Tuttle, P.C.

(57) ABSTRACT

A ventilator (1) determines states with cough attacks and an operating method for a ventilator determines cough attacks. It is determined on the basis of pressure measured values (13, 21, 19) and flow measured values (11, 15, 17) whether consecutive elevations of an airway pressure in a ventilator (1) are due to one cough event or due to a plurality of cough events. A plurality of cough events indicates a state of a cough attack. An output (41, 42, 44) of a warning (44) or alarm (42) is issued indicating the state.

27 Claims, 2 Drawing Sheets

(51) Int. Cl.
*A61B 5/097* (2006.01)
*A61B 5/00* (2006.01)
*A61M 16/08* (2006.01)

(52) U.S. Cl.
CPC ............... *A61M 2016/0027* (2013.01); *A61M 2016/0039* (2013.01); *A61M 2016/0042* (2013.01); *A61M 2205/18* (2013.01)

(56) References Cited

U.S. PATENT DOCUMENTS

| | | | | |
|---|---|---|---|---|
| 3,961,627 | A * | 6/1976 | Ernst | A61M 16/0009 128/204.21 |
| 5,400,777 | A | 3/1995 | Olsson et al. | |
| 5,937,853 | A | 8/1999 | Ström | |
| 6,308,706 | B1 * | 10/2001 | Lammers | A61B 5/087 128/204.22 |
| 2003/0221689 | A1 * | 12/2003 | Berthon-Jones | A61M 16/0057 128/204.18 |
| 2007/0199566 | A1 * | 8/2007 | Be'eri | A61M 16/0051 128/204.23 |
| 2008/0053441 | A1 * | 3/2008 | Gottlib | A61M 16/12 128/204.23 |
| 2008/0295839 | A1 * | 12/2008 | Habashi | A61M 16/0051 128/204.22 |
| 2012/0302921 | A1 * | 11/2012 | Gavriely | A61B 5/113 600/586 |
| 2013/0104899 | A1 * | 5/2013 | Friberg | A61M 16/0063 128/204.23 |
| 2014/0066725 | A1 * | 3/2014 | Mulqueeny | A61M 16/0051 600/301 |
| 2014/0150795 | A1 * | 6/2014 | Milne | A61M 16/0051 128/205.23 |
| 2019/0151585 | A1 * | 5/2019 | Troxell | A61M 16/08 |

OTHER PUBLICATIONS

All Sensors Corporation, Medical Pressure Sensor Applications, 2012, https://allsensors.com/applications.*

Stegmaier, Peter A. et al.—Fuzzy Logic Cough Detection: A First Step Towards Clinical Application.

* cited by examiner

VENTILATOR AND OPERATING METHOD FOR A VENTILATOR WITH A DETERMINATION OF COUGH ATTACKS

CROSS REFERENCE TO RELATED APPLICATIONS

This application claims the benefit of priority under 35 U.S.C. § 119 of German Application 10 2016 013 140.3, filed Nov. 7, 2016, the entire contents of which are incorporated herein by reference.

FIELD OF THE INVENTION

The present invention pertains to a ventilator (also known as a medical respirator) with a determination of states with cough attacks, as well as to an operating method for a ventilator with a determination of cough attacks.

The ventilator may be configured as a ventilator for adult patients or children, as an emergency respirator for use in rescue or search missions on land, on water or in the air, or as a special, so-called neonatal ventilator for ventilating newborns. Devices for ventilating a patient are known from the state of the art. The above-mentioned ventilators, emergency respirators, and neonatal ventilators make it possible to ventilate patients mechanically, in a mandatory or assisted manner. Ventilators are preferably used in intensive care units for treating patients, in whom the possibility of supplying breathing air and oxygen as well as of removing carbon dioxide by the patient's spontaneous breathing activity is minimized or limited.

BACKGROUND OF THE INVENTION

Ventilators for carrying out mechanical ventilation according to the state of the art are described in U.S. Pat. Nos. 2,904,035, 5,400,777, 5,937,853, and WO 2007/085110 A1.

Inadmissible operating states must be avoided for the operation of ventilators, and operating situations that could lead to inadmissible operating states must be detected as early as possible and as quickly as possible in order to avoid the possible onset of inadmissible operating states.

A method for alarm organization in a ventilator, for example, in an anesthesia apparatus or ventilator, as well as a medical device with an alarm organization during the ventilation of a patient are known from the application filed by the applicant on Jun. 16, 2016 with the application No. 10 2016 007 336.5. It is described in this application how the alarm is generated by the ventilator in case of a detected individual cough event for an alarm that indicates an elevated airway pressure, in agreement with the ISO 80601-2-12 standard, in a different manner than in case of another state of the ventilator.

Concerning the sensor system described there for pneumatic/fluidic physical states such as pressure and flow rates and the measuring sites suitable for the sensor system, this patent application 10 2016 007 336.5 shall be considered to have been included in this specification with its disclosure content by means of this reference.

The principal relationships, situations and causes necessary for understanding, in which elevations of the airway pressure may be given, shall therefore be listed here only briefly. For further details, reference should be made to the application filed by the applicant on Jun. 16, 2016 with application No. 10 2016 007 336.5 (corresponding U.S. patent application Ser. No. 15/623,815, filed Jun. 15, 2017, is hereby incorporated by reference in its entirety).

Disturbances in the dispensing of breathing gas:
  Disturbances in the flow, volume or pressure regulation are possible causes for elevations of the airway pressure. Such disturbances may be caused, for example, by mechanical or pneumatic components, such as valves or dispensing units, which have a malfunction.
Blockages in the gas supply:
  Another cause of an elevation of the airway pressure may be a compromise in the gas-carrying components. Blockages in the gas-carrying components, for example, ventilation tubes, may hinder the supply and/or removal of breathing air to or from the patient. For example, a constriction or kink in the line leading away from the patient may thus lead to the build-up of an elevated pressure in front of the kink point.
Accumulations of condensation and secretion:
  Similarly to how kink points in the tube affect the pressure conditions in the tube or at the patient, accumulations of water, which may be formed due to condensation of the humidified breathing air as well as of the moist exhaled air in the tube, may also have such an effect that an elevation of the airway pressure is possible. In addition, as possibilities for elevations of the airway pressure there are also accumulations of secretion in an endotracheal tube used for ventilation, which is introduced into the trachea of the patient via the oral cavity. Such accumulations increase the flow resistance in the endotracheal tube and thus lead to an elevation of pressure.
Counter exhalation:
  Another possibility for elevations of the airway pressure arises from situations with a so-called counter exhalation (also known as counter breathing) by the patient. Counter exhalation designates the state in which the ventilator for carrying out the mechanical ventilation delivers air to or into the patient, but the patient is attempting to exhale at the same time, i.e., to counter exhale. In this case, the patient and the ventilator are not synchronous with one another during the inspiratory (inhalation) and exhalation (expiration) phases. Such a state is rather stressful for the patient, and such a state should therefore be avoided as much as possible.
User interactions:
  Other causes for elevations of the airway pressure are setting actions performed by the user, for example, in case of changes in limit values, changes in pressure and volume values. Such user interactions may lead to pressure changes and hence to elevations of the airway pressure.
Cough events:
  Thus, an irritation of the throat may, for example, develop at the patient in certain situations, for example, due to secretion in the upper airways or in the endotracheal tube, as well as blockages in the endotracheal tube. Such an irritation of the throat or even a cough reflex is usually independent from whether the current phase of ventilation of the ventilator is an inspiratory phase (inhalation) or an expiratory phase (exhalation), and in any case it is an event during which an additional quantity of exhaled breathing gas enters the tube system with the cough abruptly, quasi as a pulse, and an increased flow rate will thus flow away from the patient. This pulse-like increase in the flow rate leads as a consequence to a massive increase in pressure or a transient pressure event occurring for a brief time. A cough or coughing fit is often observed if the secretion that is accumulated in the bronchi or the lower and upper airways triggers a cough reflex during a recovery phase, for example, after a surgical procedure. The cough reflex is usually present as long as the situation, for example, blockages in the endotracheal tube, accumulation of secretion in the endotracheal tube or in the upper airways, as well as positions of the endotracheal tube in the trachea that are uncomfortable or possibly also irritating or painful for the patient is present and lasts. In such cases, the irritation of the throat or cough reflex of individual cough events may be formed into a cough sequence or to a so-called cough attack.

Depending on the constitution and clinical picture of the patient, cough attacks may be not only be uncomfortable for the patient in unfavorable constellations, but also have an adverse effect on the healing process, as well as represent resulting dangerous situations in individual cases, if such a cough attack lasts for a rather long time. Heavy physical exertions and emotional stresses, which are detrimental to the healing progress, are, as a rule, mentioned as possible dangerous resulting situations.

Possible physical exertions are, for example, strains of the cardiovascular system with a rise in heart rate (pulse) and blood pressure.

Possible resulting dangerous situations are, for example, the undersupplying of the patient with oxygen, since the cough attacks make difficult and hinder the supply of needed quantities of fresh, oxygen-rich breathing gas.

Possible emotional stresses arise partly from the cough attacks directly as shortness of breath felt by the patient with accompanying fears of suffocation, as well as in combination with the strains of the cardiovascular system as fearful situations of a wide variety of types, for example, as situations of helplessness felt by the patient. Cough attacks are usually ended only when the causative situation is no longer present, for example, the patient has been able to eject the secretion causing the blockage by means of coughing, or when a change in the situation for the patient arises due to actions of the medical staff.

So that the medical staff can take suitable actions for changing the situation, it is advantageous that the presence of situations with cough attacks is detected during the ventilation of a patient and a corresponding alarm is outputted.

Therefore, a need arises to detect situations with cough attacks as disturbing influencing variables during the ventilation in order to thus make the ventilation as comfortable and low-risk as possible for the patient.

SUMMARY OF THE INVENTION

From this arises an object of the present invention to provide a ventilator with a determination of states with cough attacks during the operation of the ventilator.

Another object of the present invention is to provide a method for operating a ventilator with a determination of cough attacks.

According to the invention, a method is provided for operating a ventilator with a determination of cough attacks, the ventilator being configured for processing sensor signals of the ventilator provided by sensors, wherein the sensor signals indicate pneumatic/fluidic physical states of a breathing gas in a gas-carrying connection system which is connected and coupled in a gas-carrying manner to the ventilator and to a patient and is configured for transporting gases from and to the patient, from which values of an airway pressure prevailing in the gas-carrying connection system and of a flow rate, as well as of the flow directions corresponding to the flow rate in the gas-carrying connection system can be determined. The method comprises the steps of initializing an analysis time interval and a quantity of data. The method proceeds to detect the pneumatic/fluidic physical states with determination of values of pressure and flow rates as the quantity of data, to determine whether a situation of an interaction between the ventilator and the patient, with an elevated airway pressure, is present based on a comparison to determine whether a comparison criterion indicating an elevated airway pressure is exceeded by the determined value of the airway pressure and to determine whether a situation of an interaction between the ventilator and the patient is present, in which a smaller quantity of breathing gas is fed to the patient by the ventilator than flows from the patient is based on a comparison determining whether a comparison criterion indicating a flow rate and a flow direction is exceeded by the determined value of the flow rate and by the determined flow direction. The method determines whether a state, which indicates at least one cough attack, is present in the analysis time interval is based on at least one evaluation criterion, which indicates pneumatic/fluidic states of pressure, flow rate and/or volume of an interaction between the ventilator and the patient and provides a control signal, which indicates a state, which indicates a cough attack. The analysis time interval and of the quantity of data is then updated.

According to another aspect of the invention, a ventilator is provided comprising a connection system configured for transporting breathing gases. The connection system comprises an expiratory path, configured and intended for carrying an expiratory quantity of breathing gas away from the patient, an inspiratory path configured and intended for carrying an inspiratory quantity of breathing gas from the ventilator to the patient, a patient connection path configured and intended for carrying the inspiratory quantity of breathing gas from the ventilator to the patient and for carrying the expiratory quantity of breathing gas away from the patient, wherein the expiratory path and the inspiratory path are connected to one another and to the patient connection path by means of a connection element. A control unit is provided. A pressure-measuring unit, comprising at least one pressure sensor arranged in or at the ventilator or the connection system and configured and intended for detecting a pressure measured value of a pressure that is prevailing in the connection system, is configured for providing this at least one pressure measured value to the control unit as an airway pressure. A flow-measuring unit, comprising at least one flow sensor arranged in or at the connection system or in or at the ventilator and configured and intended for detecting at least one flow rate measured value of a quantity of breathing gas and a flow direction of the breathing gas corresponding to the flow rate measured value, which flows in the connection system from the patient or flows from the ventilator to the patient, is configured for providing this at least one flow rate measured value and the corresponding flow direction to the control unit. An alarm generating unit is provided. The control unit is configured for effecting an initialization of an analysis time interval and of a quantity of data and for repeatedly carrying out the following sequence of steps after the initialization of an analysis time interval and of the quantity of data: detecting of the pneumatic/ fluidic physical states with determination of values of pressure and flow rates as a quantity of data; determining whether a situation of an interaction between the ventilator and the patient with an elevated airway pressure is present based on a comparison determining whether a comparison criterion indicating an elevated airway pressure is exceeded by the determined value of the airway pressure; determining whether a situation of an interaction between the ventilator and the patient is present, in which a smaller quantity of breathing gas is fed to the patient by the ventilator than flows from the patient based on a comparison determining whether a comparison criterion indicating a flow rate and a flow direction is exceeded by the determined value of the flow rate and by the determined flow direction; determining whether a state, which indicates at least one cough attack, is present in the analysis time interval based on at least one evaluation criterion, which indicates pneumatic/fluidic states of pressure, flow rate and/or volume of an interaction between the ventilator and the patient; providing a control signal, which indicates a state, which indicates a cough attack; and updating of the analysis time interval and of the quantity of data.

Provisions are made according to the present invention for present measured values, signals from sensors, which are also called sensor signals, in a ventilator, which is suitable and configured for ventilating a patient or living being, being used to detect whether states are present, which indicate cough attacks.

The ventilator, on which the method for operating a ventilator with a determination of cough attacks is carried out, is preferably configured as a ventilator suitable for long-term ventilation for use in an intensive care unit in a hospital.

Disturbances in the supply and in the removal of breathing gases from the airways of a patient arise at the pneumatic/fluidic port, e.g., in the endotracheal tube or at the transition of the endotracheal tube due to accumulations of viscous liquids, for example, secretion or even blood, that are present there. Such blockages or accumulations of viscous fluids increase the flow resistance in the endotracheal tube and may thus lead to an elevation of the airway pressure $P_{AW}$. This results in a triggering of an irritation of the throat or cough reflex with the result that a cough event occurs, which is superimposed to the normal rhythm of inhalation and exhalation as a transient elevation of the airway pressure $P_{AW}$ in combination with a short-term increase in the flow rate $\dot{V}_{Pat}$ exhaled by the patient. A positioning of the endotracheal tube in the pharynx that is uncomfortable for the patient may also cause an irritation in the trachea, which may trigger cough reflexes.

A clustering of a plurality of cough events within a short time of one another, for example, in a time interval of less than one second up to a few seconds indicates a state of a cough attack. Situations in which a plurality of cough events is triggered due to external effects, for example, irritations, especially skin irritations, can be caused in the area of the trachea or of the pharynx, which may be caused by a position of an endotracheal tube in the upper airways (bronchi, trachea) of the patient that is uncomfortable for the patient, are mentioned as states which indicate cough attacks.

Such cough attacks with a plurality of elevations of the flow rates $\dot{V}_{Pat}$ exhaled by the patient result, taking a time interval into consideration, in a volume $V_{Pat}$ above the tidal volume $V_T$ typical for the patient, which can be balanced in the time interval.

Signals of sensors are available for the analysis for analyzing the situation and for differentiating whether a cough attack of the patient is cause for an elevation of the airway pressure $P_{AW}$ or for a short-term elevation of the flow rate $\dot{V}_{Pat}$ exhaled by the patient. These sensors are, for example, pressure sensors and flow sensors, which are located in or at the ventilator or are arranged at this device in or at gas-carrying components or connection systems, such as, for example, tube systems.

Measuring sites in or at the ventilator, at which pressure measurements and flow measurements can be carried out and from which it is possible to determine both the airway pressure and the patient's flow rate, are an inspiratory measuring site and an expiratory measuring site within or at the ventilator for the mechanical ventilation of a patient, as well as a measuring site (Y-piece) located close to the patient, outside and proximally to the ventilator, for example, in or at the gas-carrying components or connection systems.

Three suitable measuring sites for pressure measurement and flow measurement, which are different, in principle, from one another, an inspiratory measuring site and an expiratory measuring site within the ventilator for ventilating a patient, as well as a measuring site (Y-piece) located close to the patient, outside and proximally to the ventilator for ventilating a patient are mentioned in Table 1 below. The measured values that can be obtained at these measuring sites as well as the measured variables that can be derived, calculated or determined from these are shown.

TABLE 1

| Measuring site | Detected measured pressure value | Determinable pressure measured variable | Detected measured flow value | Determinable measured flow variable |
|---|---|---|---|---|
| Inspiratory (inhalation) | Inspiratory pressure $P_{insp}$ | $P_{aw} = P_{insp} - P_{hose\_insp}$ | Inspiratory flow rate $\dot{V}_{insp}$ | $\dot{V}_{Pat} = \dot{V}_{exp} - \dot{V}_{insp}$ |
| Expiratory (exhalation) | Expiratory pressure $P_{exp}$ | $P_{aw} = P_{exp} + P_{hose\_exp}$ | Expiratory flow rate $\dot{V}_{exp}$ | |
| Close to the patient (proximal) | Patient pressure $P_{Pat}$ | $P_{aw} = P_{Pat}$ | Patient flow rate $\dot{V}_{Pat}$ | $\dot{V}_{Pat}$ Quantity & direction |

In Table 1 above, $P_{aw}$=airway pressure, $P_{Pat}$=estimated pressure in the lungs of the patient on the basis of the pressure measured close to the patient, $P_{insp}$=inspiratory pressure at the inhalation outlet of the ventilator, $P_{exp}$=expiratory pressure at the exhalation inlet of the ventilator, $P_{hose\_insp}$=pressure gradient at the inspiratory ventilation tube, $P_{hose\_exp}$=pressure gradient at the expiratory ventilation tube, $\dot{V}_{Pat}$=flow rate at the patient, $\dot{V}_{exp}$=expiratory flow rate into the exhalation inlet of the ventilator, $\dot{V}_{insp}$=inspiratory flow rate from the inhalation outlet of the ventilator.

According to a first aspect of the present invention, the object is accomplished by a method according to the present invention for determining states, which indicate cough attacks of a patient.

The method according to the present invention is configured for detecting states, which indicate cough attacks of a patient during an interaction between a patient and a ventilator, and for providing an output of a control signal indicating a state of a cough attack for generating an alarm based on these detected states with cough attacks.

The ventilator is configured for processing sensor signals arranged in or at the ventilator or provided with sensors connected to the ventilator. The sensor signals indicate pneumatic/fluidic physical states of a breathing gas in a gas-carrying connection system from and to the patient, which the system is connected and coupled to the ventilator and to a patient in a gas-carrying manner and is configured for transporting gases. In this case, the connection system is preferably configured as a ventilation tube, more preferably as a combination of an inspiratory ventilation tube and an expiratory ventilation tube. As an alternative thereto, a coaxial ventilation tube system, as well as a so-called "one-tube system" may be used.

Values of an airway pressure $P_{AW}$ that are currently present in the gas-carrying connection system and of a flow rate flowing in the gas-carrying connection system, as well as flow directions corresponding to the flow rate in the gas-carrying connection system may be determined from the sensor signals.

The method for determining states, which indicate cough attacks, according to the present invention uses these sensor signals for determining the airway pressure $P_{AW}$, as well as for determining, evaluating and classifying states and situations, as well as operating states in the gas-carrying connection system and/or ventilator. In this case, temporary elevations of the airway pressure $P_{AW}$ as well as elevations of the flow rates $\dot{V}_{Pat}$ exhaled by the patient are identified as cough events in the method according to the present invention by means of analyzing signals of the pressure sensors and flow sensors. A plurality of cough events occurring in a sequence within a short time of one another are evaluated as a state, which indicates a cough attack, in the method according to the present invention.

Based on this, a control signal indicating this state is provided in the method according to the present invention. This control signal is provided or outputted for generating an alarm of the state, which indicates a cough attack.

In the method according to the present invention for determining states with cough attacks in a ventilator, the following steps are carried out in a repeating sequence of steps after an initialization of an analysis time interval and of a quantity of data:

detection of the pneumatic/fluidic physical states with determination of values of pressure and flow rates as a quantity of data, determination whether a situation of an interaction between the ventilator and the patient with an elevated airway pressure is present on the basis of a comparison whether a comparison criterion indicating an elevated airway pressure is exceeded by the determined value of the airway pressure, determination whether a situation of an interaction between the ventilator and the patient is present, in which a smaller quantity of breathing gas is fed to the patient by the ventilator than flows from the patient on the basis of a comparison whether a comparison criterion indicating a flow rate and a flow direction is exceeded by the determined value of the flow rate and by the determined flow direction, determination whether a state, which indicates at least one cough attack, is present in the analysis time interval on the basis of at least one evaluation criterion, which indicates pneumatic/fluidic states of pressure, flow rate and/or volume of an interaction between the ventilator and the patient, provision of a control signal (generating a control signal), which indicates the state, which indicates a cough attack, updating of the analysis time interval and of the quantity of data.

The quantity of data is selected corresponding to the analysis time interval. When the analysis time interval and the quantity of data are initialized, a need sufficient for the analysis and for the duration of the analysis time interval is kept ready in a memory and the chronological starting point of the analysis time interval is set before the beginning of the continuous carrying out of the method for determining states with cough attacks. The analysis time interval is updated over the course of time of the detection with the chronological progress of the detection, so that a sliding time interval arises, which is characterized in that the chronologically most current pressure and flow rate values are incorporated into the quantity of data for determining the state, which indicates at least one cough attack, and the chronologically oldest pressure and flow rate values are no longer included in the quantity of data for determining the state which indicates at least one cough attack. When the analysis time interval and the quantity of data are updated, the analysis time interval and the corresponding quantity of data are updated by a predefined time interval or a predefined number of pressure and flow rate values over the course of time of the detection. This occurs, for example, by means of a shifting in the quantity of data by one or more scanned values of the pressure and flow rate values over the course of time.

The situation, in which a greater quantity of breathing gas is fed or flows towards the patient from the ventilator by means of the inspiratory connection system (inspiratory ventilation tube) than flows from the patient, corresponds here to the inspiratory phase (inhalation).

The situation, in which a smaller quantity of breathing gas is fed or flows to the patient by way of the ventilator by means of the inspiratory connection system than flows from the patient and, for example, flows back into the ventilator via an expiratory connection system, corresponds here to the expiratory phase (exhalation).

The situation of the interaction between the ventilator and the patient, in which a smaller quantity of breathing gas is fed by the ventilator to the patient than flows from the patient, usually corresponds to a expiratory phase (exhalation), or to a time of an at least short-term exhalation, and to a cough event in conjunction with the elevation of the airway pressure in cases, in which the elevation of the airway pressure $P_{AW}$ cannot be attributed directly to disturbances involved with the dispenser or user interactions.

There are situations in both inspiratory phases (inhalation) and in expiratory phases (exhalation) in which additional quantities of exhaled breathing gas are present as at least temporary elevations of the flow rate in the gas-carrying connection system (ventilation tube) and lead to elevations of the airway pressure $P_{AW}$ due to a cough event or a plurality of cough events or cough sequences.

These at least temporary elevations of the airway pressure $P_{AW}$ with a simultaneity of the interaction between the ventilator and the patient, in which a smaller quantity of breathing gas is fed by the ventilator to the patient than flows from the patient, as an indicator of states with cough attacks are determined on the basis of the sensor signals of the sensors arranged at the measuring sites of the ventilator or at the gas-carrying connection system.

In situations of the interaction between the ventilator and the patient, in which a state is present, which indicates a cough attack, a control signal or an output, which indicates this state, is provided and/or outputted by the ventilator.

For example, this may be a signal, which makes possible an output of a warning, a message, an acoustic alarm or a visual alarm to the medical staff directly at the ventilator.

Such a control signal may, however, also be transmitted to a remote unit for outputting alarms and messages, for example, in the nurses' station, or to a mobile data output system (pager, mobile phone) by means of suitable and usual data transmission channels (telephone, SMS, LAN, WLAN, network, Bluetooth®).

Signals of at least one pressure sensor, whose signals indicate the at least temporary elevations of the airway pressure $P_{AW}$, are preferably used as a basis for the values for determining the airway pressure $P_{AW}$ in the method for determining states with cough attacks during the operation of the ventilator.

This at least one pressure sensor is preferably arranged at the connection system, located close to the mouth/nose area of the patient at the patient connection path or at the connection element (Y-piece).

Further, the at least one pressure sensor or an additional pressure sensor is preferably arranged at the inspiratory connection system. Further, the at least one pressure sensor or an additional pressure sensor is preferably arranged at the expiratory connection system.

A predefined pressure threshold value is preferably selected in another embodiment to be a possible comparison criterion, which indicates an elevated airway pressure $P_{AW}$. Thus, for example, a pressure value above the pressure threshold value, for example, from 30 hPa+3 hPa, characterizes an elevated airway pressure for an adult patient, as well as for an adolescent or pediatric patient in a comparable manner. A pressure value above a pressure threshold value of 20 hPa+1 hPa characterizes, for example, an elevated airway pressure for an infant patient.

In another preferred embodiment of the method, the determination whether a smaller quantity of breathing gas is fed by the ventilator to the patient than flows from the patient due to the interaction between the ventilator and the patient is determined on the basis of a comparison whether a comparison criterion indicating a flow rate and a flow direction is exceeded by the determined value of the flow rate and by the determined flow direction.

A possible comparison criterion, which indicates the flow rate and the flow direction, is a predefined flow rate threshold value connected with a flow direction. Thus, for example, a flow rate above a flow threshold value, for example, from about 2.5 L/min±0.2 L/min, with a corresponding flow direction away from the patient characterizes an exhalation (expiration). Thus, for example, a flow rate above a flow threshold value, for example, from 1.5 L/min±0.2 L/min, with a corresponding flow direction towards the patient characterizes an inhalation (inspiration). Thus, a flow rate below a flow threshold value, for example, from 2.5 L/min±0.2 L/min, with a corresponding flow direction away from the patient characterizes an end of an expiration or an expiratory pause. Thus, for example, a flow rate below a flow threshold value, for example, from 1 L/min±0.2 L/min, with a corresponding flow direction towards the patient characterizes a beginning or an end of an inspiration or an inspiratory pause.

These flow rates are determined on the basis of the sensor signals of the sensors arranged at the measuring sites of the ventilator or at the gas-carrying connection system.

For this, signals of at least one flow sensor, the signals of which indicate the flow rates and flow directions in the connection system, are preferably used in the method for determining states with cough attacks during the operation of the ventilator.

This at least one flow sensor is preferably arranged at the connection system located close to the mouth/nose area of the patient at the patient connection path or at the connection element (Y-piece).

Further, the at least one flow sensor or another flow sensor is preferably arranged at the inspiratory connection system.

Further, the at least one flow sensor or another flow sensor is preferably arranged at the expiratory connection system.

In another preferred embodiment of the method, at least information from a course of the control of the ventilator concerning the current phase of breathing or information concerning a state of an expiratory valve or an actuating signal for such an expiratory valve is taken into account for determining whether a smaller quantity of breathing gas is fed by the ventilator to the patient than flows from the patient and thus an indicator of states with cough attacks are present due to the interaction between the ventilator and the patient. By means of the control of the expiratory valve during the mechanical, for example, mandatory or assisted ventilation, the ventilator causes the continuous course of expiratory phases (exhalation) and inspiratory phases (inhalation) on the basis of the respiration rate (RR) and of the inspiration time to expiration time ratio (I:E ratio). Thus, in many situations, at least information concerning the current phase of breathing can be derived from the state and the control of the expiratory valve. It is possible with this information on the state of the valve (closed, opened, degree of setting) to verify, especially during ventilation with mandatory ventilation modes, from the course of the control whether a smaller quantity of breathing gas is fed to the patient than flows from the patient, i.e., whether an expiratory phase (exhalation), usually preset mandatorily by the medical device, is present as far as the medical device is concerned.

In a preferred embodiment of the method, the analysis time interval is preferably selected here in a range of 20 sec to 60 sec or in a range of 1 or 2 to 5 consecutive breathing cycles. Such an analysis time interval of seconds 20 sec to 60 sec—usually comprises in this case a number of about three to six cough events, which, taken together, represent a cough attack. A time limitation of the analysis time interval to a preferable range of 20 sec to 40 sec or to a number of at most four consecutive breathing cycles may be helpful depending on the cough behavior of the patient in order to determine states with cough attacks with less time delay.

An analysis of the cough events for an identification of cough attacks can be carried out in this case in a variety of ways, which, each in itself, as well as combined, makes possible the determination of the state, which indicates a cough attack. At least one evaluation criterion from the following list of evaluation criteria, which indicate pneumatic/fluidic physical states of an interaction between the ventilator and the patient, is used for the analysis.

a. Evaluation criterion: Number of cough events, based on pressure

When a predefined minimum number of cough events occur in an analysis time interval with a predefined duration $T_a$ by means of elevations of the airway pressure $P_{AW}$ above a predefined pressure threshold value selected as the comparison criterion, then this is assessed such that a state is present, which indicates a cough attack. The counting of the number of individual pressure elevations based on cough events in the analysis time interval results in an indicator of the frequency of cough events in the analysis time interval as a basis for evaluating that a state is present, which indicates a cough attack.

b. Evaluation criterion: Number of cough events, based on flow rate

When a predefined minimum number of cough events occur in an analysis time interval with a predefined duration $T_b$ by means of elevations of the flow rates $\dot{V}_{Pat}$ exhaled by the patient above a predefined flow threshold value selected as the comparison criterion, then this is assessed such that a state is present, which indicates a cough attack.

The counting of the number of individual flow rate elevations based on cough events in the analysis time interval results in an indicator of the frequency of cough events in the analysis time interval as a basis for evaluating that a state is present, which indicates a cough attack.

c. Evaluation criterion: Weighting of cough events

When in an analysis time interval with a predefined duration $T_c$, an integral over time from determined pressure values, which indicate elevations of the airway pressure $P_{AW}$, i.e., for example, a time integral of all pressure values above a predefined pressure threshold value, exceeds a predefined pressure integral threshold value in the analysis time interval, then this is assessed such that a state is present, which indicates a cough attack. The formation of the time integral over the pressure values of the airway pressure $P_{AW}$ results here in a pressure integral, which can be called a "pressure-specific cough effect," since the effects of a plurality of individual pressure elevations of different durations and with different pressure level or pressure peak value, rather than the exact number of cough events themselves are summed up over the course of the ventilation. In this connection, the pressure integral may be considered to be a type of summary effect of elevations of the airway pressure $P_{AW}$.

d. Evaluation criterion: Weighting of cough events, based on volume

When in an analysis time interval with a predefined duration $T_d$ an integral over time from determined flow rate values, which indicate elevations of the flow rates, i.e., for example, a time integral of all flow rates above a predefined flow rate threshold value, exceeds a predefined flow integral threshold value in the analysis time interval, then this is assessed such that a state is present, which indicates a cough attack. This thus results in an evaluation based on "cough volumes" on the basis of cough events, which were determined by means of elevations of the flow rates $\dot{V}_{Pat}$ exhaled by the patient. The formation of the time integral over the flow rate values results in this case in a volume, which can be called a "flow-specific cough volume," since only volume portions are summed up over the course of the ventilation, flow rates are present as elevations of the airway pressure $P_{AW}$.

e. Evaluation criterion: Weighting of cough events, based on pressure

When in an analysis time interval with a predefined duration $T_e$ an integral over time from determined flow rate values, which correspond to determined pressure values over time, which indicate elevations of the airway pressure, i.e., for example, a time integral of all flow rates above a predefined flow rate threshold value, exceeds a predefined flow integral threshold value in the analysis time interval, then this is assessed such that a state is present, which indicates a cough attack. In this connection, one or more cough events, which were determined on the basis of the airway pressure $P_{AW}$, with respect to the state whether these identified cough events together result in a cough attack, in relation to the volumes $\dot{V}_{Pat}$ exhaled by the patient resulting due to the cough events, are evaluated. This thus results in an evaluation based on "cough volumes" on the basis of cough events that were determined by means of elevations of the airway pressure $P_{AW}$. The formation of the time integral over the flow rate values results here in a volume, which can be called a "pressure-specific cough volume," since only those "volume portions" over the course of the ventilation are summed up by means of the integral, at which simultaneous elevations of the airway pressure $P_{AW}$ over time are present.

The following preferred embodiments describe embodiments using the evaluation criteria according to the list (a.-e.) of evaluation criteria.

In one preferred embodiment of the method, a comparison with a predefined minimum number of cough events in the analysis time interval, for example, a number of 4 to 6 cough events is used as at least one evaluation criterion for analysis whether a state is present, which indicates a cough attack.

In another preferred embodiment of the method, a comparison with a predefined minimum number of cough events, for example, a number of four or more cough events, on the basis of elevations of the airway pressure $P_{AW}$ above the predefined pressure threshold value, is used as at least one evaluation criterion for analysis whether a state is present, which indicates a cough attack, in the analysis time interval. The predefined pressure threshold value for determining the cough events is in this case preferably selected in a range of 30 hPa±3 hPa for adults, adolescents or children, or in a range of 20 hPa±1 hPa for infants and/or toddlers.

In another preferred embodiment of the method, a comparison with a predefined minimum number of cough events, for example, an exceeding of a number of at least 4 to 6 cough events, on the basis of elevations of the flow rates $\dot{V}_{Pat}$ exhaled by the patient above the predefined flow rate threshold value is used as at least one evaluation criterion for analysis whether a state is present, which indicates a cough attack, in the analysis time interval. The predefined flow rate threshold value for determining the cough events may in this case be selected as a threshold value in a range of 90 L/min to 180 L/min, for example, a flow rate above 120 L/min. The analysis time interval is in this case preferably selected in a range of 20 sec to 60 sec or in a range of 2 to 5 consecutive breathing cycles.

In a preferred embodiment of the method, a summary effect of individual cough events, i.e., events with corresponding elevations of the airway pressure $P_{AW}$ above the predefined pressure threshold value, by means of a formation of a time integral of the elevations of the airway pressure $P_{AW}$ in the analysis time interval, is used as at least one evaluation criterion for analysis whether a state is present, which indicates a cough attack. An exceeding of a predefined effect threshold value due to the cough events is assessed here as an indicator of the state of a cough attack. In this case, this predefined effect threshold value may be used, for example, in units of pressure (hPa, mbar) or as a dimensionless numerical value. For this, a multiple, e.g., 3 times to 5 times the pressure threshold value is preferably selected. The analysis time interval is preferably selected here in a range of 20 sec to 60 sec or in a range of 2 to 5 consecutive breathing cycles.

In a preferred embodiment of the method, a minimum quantity of a flow rate in the analysis time interval, corresponding to a minimum volume, which flows from the patient due to cough events in the analysis time interval, is used as at least one evaluation criterion for analysis whether a state is present, which indicates a cough attack.

In another preferred embodiment of the method, a summary effect of individual cough events, i.e., events with corresponding elevations of the flow rates $\dot{V}_{Pat}$ exhaled by the patient above the predefined flow rate threshold value, by means of a formation of a time integral of the elevations of the flow rates $\dot{V}_{Pat}$ exhaled by the patient in the analysis time interval, is used as at least one evaluation criterion for analysis whether a state is present, which indicates a cough attack. The predefined flow rate threshold value for determining the cough events is selected here in a preferable range of 90 L/min to 180 L/min. An exceeding of a predefined minimum volume or of a predefined volume threshold value due to the cough events is assessed here as an indicator of the state of a cough attack.

The predefined minimum volume may in this case be selected in relation to the tidal volume $V_T$ or to the minute volume MV of the patient, for example, an integral volume of 10%-20% above the tidal volume $V_T$ or a sudden exceeding of the previously balanced minute volume by 5% to 10% may be selected as a volume threshold value. The exceeding of the predefined minimum volume may also be determined by means of an exceeding of a predefined volume threshold value as a volume value, which, for example, corresponds to at least 3 times to 5 times a typical tidal volume. With a typical tidal volume of 0.5 L+0.2 L, possible values of about 1 L to 3 L then arise for the minimum volume as well as for the volume threshold value. The analysis time interval is selected here in a range of 20 sec to 60 sec or in a range of 2 to 5 consecutive breathing cycles.

In a preferred embodiment of the method, a summary effect of individual cough events, i.e., events with corresponding elevations of the airway pressure $P_{AW}$ above a predefined pressure threshold value, by means of a formation of a time integral of the elevations of the flow rates corresponding to the cough events in the analysis time interval, is used as at least one evaluation criterion for analysis whether a state is present, which indicates a cough attack. The predefined pressure threshold value for determining the cough events is preferably selected here in a range of 30 hPa+3 hPa for adults, adolescents or children, or in a range of 20 hPa+1 hPa for infants and/or toddlers. The predefined volume threshold value may also be selected here in relation to the tidal volume $V_T$ or the minute volume MV of the patient, for example, an integral volume of 10%-20% above the tidal volume or a sudden exceeding of the previously balanced minute volume by 5% to 10% may be selected as the volume threshold value. The predefined volume threshold value may also be selected as a volume value, which, for example, corresponds to at least 3 times a typical tidal volume. With a typical tidal volume of 0.5 L+0.2 L, possible values of about 1 L to 3 L then arise for the volume threshold value. The analysis time interval is preferably selected here in a range of 20 sec to 60 sec or in a range of 2 to 6 consecutive breathing cycles.

The embodiments described represent special embodiments of the method according to the present invention for determining states with cough attacks in a ventilator during the operation of the ventilator in themselves as well as in combination or combinations with one another. In this case, all and possible additional embodiments arising through a combination or combinations of a plurality of embodiments and their advantages are likewise covered by the idea of the present invention, even though not all possibilities of combining embodiments are specifically described for this in detail.

The above-described embodiments of the method according to the present invention may also be configured in the form of a computer-implemented method as a computer program product with a computer, wherein the computer is prompted to execute the above-described method according to the present invention, when the computer program is executed on the computer or on a processor of the computer or on a so-called "embedded system" as part of a medical device. In this case, the computer program may also be stored on a machine-readable storage medium. In an alternative embodiment, a storage medium, which is intended for storing the above-mentioned, computer-implemented method and can be read by a computer, may be provided. It is within the scope of the present invention that not all steps of the method have necessarily to be executed on one and the same computer, but rather they may also be executed on different computers. The sequence of the method steps may possibly also be varied. It is furthermore possible that individual sections of the above-described method can be executed in a separate unit, which can be sold, for example, by itself.

The solution for accomplishing the object was described above with respect to the method claimed as a first aspect of the present invention. In addition, a ventilator, which is configured to carry out the method according to the present invention in the sense of at least one of the embodiments described, arises as another aspect.

Features mentioned for the method, described advantages or alternative embodiments can likewise be applied to the other claimed subjects as well and vice versa. The corresponding functional features of the method are configured here by hardware components (µC, µP, DSP, FPGA, ASIC, GAL, logical units), which may be implemented, for example, in the form of a processor (µP), a plurality of processors or in the form of instructions in an internal or external memory or memory area, which are processed by the processor.

The advantages described for the method according to the present invention can be achieved in the same or a similar manner with the ventilator according to the present invention. Furthermore, the described embodiments and their features and advantages of the method can be applied to the ventilator, and the described embodiments of the ventilator can be applied to the method.

The object of determining states, which indicate cough attacks of a patient, is also accomplished according to the present invention by a ventilator according to the additional aspect of the present invention.

This ventilator is configured for a mechanical, mandatory or assisted ventilation of a patient and has for this, according to the present invention, a connection system configured for transporting breathing gases, a pressure-measuring unit, a flow-measuring unit, a control unit, a dispensing unit and an alarm generation unit. The control unit is preferably configured here as a microprocessor module (µC) with associated internal and/or external memory (RAM). The flow-measuring unit as well as the pressure-measuring unit are configured for converting electrical signals, which indicate physical measured variables and which are provided by the flow rate sensors and pressure sensors, into data signals suitable for data processing. In the usual configurations of anesthesia apparatuses and ventilators, the flow-measuring unit, the pressure-measuring unit and the alarm generation unit are configured as components or modules of the control unit.

The connection system has an expiratory path, which is configured and intended for removing an expiratory quantity of breathing gas from the patient. The connection system has an inspiratory path, which is configured and intended for feeding an inspiratory quantity of breathing gas to the ventilator. The connection system has a patient connection path, which is configured and intended for feeding the inspiratory quantity of breathing gas from the ventilator to the patient and for removing the expiratory quantity of breathing gas from the patient. The expiratory path and the inspiratory path are connected to one another and to the patient connection path by means of a connection element. The connection element may be and is often configured in practice as a so-called Y-piece.

The flow-measuring unit has at least one flow sensor, which is arranged in or at the connection system or in or at the ventilator and is intended for detecting at least one flow rate of a quantity of breathing gas that is flowing away from the patient in the connection system or is flowing from the ventilator to the patient. The flow-measuring unit is configured to provide this at least one flow rate measured value to the control unit.

The pressure-measuring unit has at least one pressure sensor, which is arranged in or at the ventilator or at the connection system and is intended for detecting a measured value of a pressure, which is present in the connection system, and the pressure-measuring unit is configured to provide this at least one pressure measured value to the control unit.

The control unit is configured in a suitable manner, preferably by means of an interface, to receive pressure measured values and flow measured values, preferably from the pressure-measuring unit and from the flow-measuring unit, or to input them via a data link. The control unit is configured in a suitable manner for comparing the detected pressure measured value with a predefined pressure threshold value. The control unit is configured in a suitable manner in conjunction with the dispensing unit to control or regulate an array of valves in a suitable manner in order to allow a course of a ventilation with pressure control or volume control, limit value monitoring for pressures and volumes with the selection of a respiration rate and durations (I:E) of the inspiratory phases (inhalation) and expiratory phases (exhalation) to take effect by means of the ventilator at the patient. The control unit is further configured to compare the at least one detected flow rate measured value with a predefined flow rate threshold value and to determine on the basis of the comparison whether the at least one flow rate measured value exceeds a predefined flow rate threshold value. The control unit is further configured to determine whether the at least one flow rate measured value and the corresponding flow direction indicate a situation of a phase of an exhalation (expiration) with a flow rate and with a flow direction corresponding to the flow rate, in which the quantity of breathing gas flowing towards the patient is smaller than the quantity of breathing gas flowing away from the patient is present. The pressure and flow threshold values are in this case preferably provided directly to the control unit or, as an alternative, indirectly with involvement of the memory.

An alternative possibility for determining the situation of the interaction between the ventilator and the patient, in which a smaller quantity of breathing gas is fed or flows by way of the ventilator towards the patient by means of the inspiratory path of the connection system than flows from the patient by means of the one expiratory path of the connection system, arises for the control unit from the utilization of information from the course of the ventilation with a control of inspiratory phases (inhalation), expiratory phases (exhalation), volumes ($V_T$) and ventilation pressures ($P_{insp}$, Pexsp, PEEP).

The control unit is thus configured to determine when a situation of the interaction between the ventilator and the patient is present, in which a smaller quantity of breathing gas is fed or flows by the ventilator to the patient by means of the inspiratory path of the connection system than flows from the patient by means of the one expiratory path of the connection system. This situation corresponds in this case to a state of an exhalation, i.e., to an expiratory phase of the patient, in which, due to a cough event, an additional quantity of exhaled breathing gas as an at least temporary increase in the flow rate in the gas-carrying connection system is present and the predefined pressure threshold value was caused to be exceeded due to the cough event or coughing fit.

Therefore, according to the present invention, the control unit is further prepared and configured to determine situations in which the at least one flow rate measured value exceeds the predefined flow rate threshold value and the detected pressure measured value exceeds the predefined pressure threshold value as cough events and to determine a state, which indicates at least one cough attack, by including an evaluation criterion.

The control unit is further configured, in combination with the memory, to continuously detect a plurality of flow rate measured values and a plurality of pressure measured values as elements of a quantity of data in an analysis time interval. In this case, the analysis time interval is updated by the control unit as a sliding time interval over the course of time of the detection with the progress over time of the detection, so that the most current pressure and flow rate values over the course of time are incorporated into the quantity of data for an analysis by the control unit, and the oldest pressure and flow rate values are no longer included as quantity of data in the analysis by the control unit.

The control unit is further configured to provide a control signal, which indicates the state of a cough attack of the patient, at an interface, for example, for transmission into a data network (LAN, WLAN).

The control unit is further configured for activating and/or deactivating the alarm generation unit for an output of an alarm generation of a visual and/or acoustic warning or alarm, indicating the state, which indicates a cough attack of the patient.

The ventilator determines by means of the control unit the state, which indicates a cough attack of the patient, wherein the control unit is configured to effect an initialization of an analysis time interval and of a quantity of data and after initialization of the analysis time interval and of the quantity of data, to repeatedly carry out the following sequence of steps:

detection of the pneumatic/fluidic physical states with determination of values of pressure and values of flow rates as a quantity of data, determination whether a situation of an interaction between the ventilator and the patient with an elevated airway pressure is present on the basis of a comparison whether a comparison criterion indicating an elevated airway pressure is exceeded by the determined value of the airway pressure, determination whether a situation of an interaction between the ventilator and the patient is present, in which a smaller quantity of breathing gas is fed to the patient by the ventilator than flows from the patient on the basis of a comparison whether a comparison criterion indicating a flow rate and a flow direction is exceeded by the determined value of the flow rate and by the determined flow direction, determination whether a state, which indicates at least one cough attack, is present in the analysis time interval on the basis of at least one evaluation criterion, which indicates pneumatic/fluidic physical states of pressure, flow rate and/or volume of an interaction between the ventilator and the patient, provision of a control signal, which indicates the state, which indicates a cough attack, updating of the analysis time interval and of the quantity of data.

The quantity of data is selected and kept ready in the memory as a quantity at a memory location, corresponding to the duration of the analysis time interval.

When the analysis time interval and the quantity of data are initialized, this quantity is kept ready by the control unit at the memory location in the memory and the chronological starting point of the analysis time interval is set before the beginning of the continuous carrying out of the sequence of steps for determining states with cough attacks.

Over the course of time of the detection with the progress of the detection over time, the analysis time interval is updated by the control unit, so that a sliding time interval arises, which is characterized in that the most current pressure and flow rate values kept ready in the memory are incorporated into the quantity of data for determination of the state, which indicates at least one cough attack, and the oldest pressure and flow values are no longer addressed in the memory by the control unit or can no longer be addressed by the control unit and thus are no longer included by the control unit in the analysis of the quantity of data for determining the state, which indicates at least one cough attack.

When the analysis time interval and the quantity of data are updated, the analysis time interval and the corresponding quantity of data are updated by the control unit by a predefined time interval or by a predefined number of pressure and flow rate values over the course of time of the detection. This occurs, for example, by means of a shifting of the data within the quantity of data in the memory or by changing an address pointer to memory areas in the memory by the control unit by one or more scanned values of the pressure and flow rate values over the course of time.

In a preferred embodiment of the ventilator, the at least one pressure sensor or another pressure sensor is arranged and configured for detecting and determining the pressure at the connection element (Y-piece), which is configured by means of suitable signal/data lines for transmitting a signal of the pressure value to the control unit.

In a preferred embodiment of the ventilator, the at least one pressure sensor or another pressure sensor is arranged and configured for detecting the pressure at the inspiratory connection system (ventilation tube), which is configured by means of suitable signal/data lines for transmitting a signal of the pressure value to the control unit.

In a preferred embodiment of the ventilator, the at least one pressure sensor or another pressure sensor is arranged at the expiratory connection system (ventilation tube) for detecting the pressure, which is configured by means of suitable signal/data lines for transmitting a signal of the pressure value to the control unit.

In a preferred embodiment of the ventilator, at least one flow sensor for detecting flow rates and flow directions is arranged at the patient connection path or at the connection element (Y-piece), which is configured by means of suitable signal/data lines for transmitting a signal of the flow rate values to the control unit.

The flow rate values indicate at least the flow rates flowing from the patient, preferably also the flow rates flowing to the patient.

The control unit is configured for determining whether the ventilator is located in a situation of the interaction between the ventilator and the patient, in which a smaller quantity of breathing gas is fed by the ventilator to the patient than flows from the patient on the basis of the signal of the flow sensor arranged at the patient connection path or at the connection element (Y-piece).

In a preferred embodiment of the ventilator, at least one flow sensor or another flow sensor is arranged at the inspiratory connection system (ventilation tube), which is configured by means of suitable signal/data lines for transmitting a signal of the flow rate values to the control unit. The flow rate values indicate the flow rates flowing to the patient.

In a preferred embodiment of the ventilator, at least one flow sensor or another flow sensor is arranged at the expiratory connection system (ventilation tube), which is configured by means of suitable signal/data lines for transmitting a signal of the flow rate values to the control unit. The flow rate values indicate the flow rates flowing from the patient.

In another preferred embodiment, the control unit is configured for determining whether the ventilator is located in a situation of the interaction between the ventilator and the patient, in which a smaller quantity of breathing gas is fed by the ventilator to the patient than flows from the patient on the basis of a difference from the signals of the flow sensor arranged in or at the expiratory path of the connection system and of the flow sensor arranged in or at the inspiratory path of the connection system.

In another preferred embodiment of the ventilator, the control unit takes into account information from a course of the control of the ventilator concerning the current breathing phase or information concerning the state of an expiratory valve or an actuating signal for such an expiratory valve for determining whether a smaller quantity of breathing gas is fed by the ventilator to the patient than flows from the patient and thus an indicator of states with cough attacks are present due to the interaction between the ventilator and the patient. By means of the control of the expiratory valve during the mechanical, for example, mandatory or assisted ventilation, the control unit causes the continuous course of expiratory phases (exhalation) and inspiratory phases (inhalation) on the basis of the respiration rate (RR) and of the inspiration time to expiration time ratio (I:E ratio). Thus, in many situations, at least information concerning the current phase of breathing can be derived from the state and the control of the expiratory valve. It is possible with such information on the state of the valve (closed, opened, degree of setting) for the control unit to verify, especially during ventilation with mandatory ventilation modes, from the course of the control whether a smaller quantity of breathing gas is fed by the medical device to the patient than flows from the patient, i.e., whether a expiratory phase (exhalation), usually preset mandatorily by the medical device, is present as far as the medical device is concerned.

In another embodiment, a predefined pressure threshold value is selected by the control unit as a possible comparison criterion, which indicates an elevated airway pressure $P_{AW}$. Thus, for example, a pressure value above a pressure threshold value, for example, of 30 hPa+3 hPa, characterizes an elevated airway pressure for an adult patient. Thus, for example, a pressure value above a pressure threshold value of 20 hPa+1 hPa characterizes an elevated airway pressure for an infant patient.

In a preferred embodiment, the control unit is configured to select a time range of 20 sec to 60 sec or a number of 2 to 6 consecutive breathing cycles as an analysis time interval.

In a preferred embodiment, the control unit is configured to use a minimum number of cough events, for example, a number of at least 4 to 6 cough events in the analysis time interval as at least one evaluation criterion whether a state is present, which indicates a cough attack.

In another preferred embodiment, the control unit is configured to use a predefined minimum number of cough events, for example, a number of 4 to 6 cough events, on the basis of elevations of the airway pressure $P_A$, above the predefined pressure threshold value as at least one evaluation criterion for analysis whether a state is present, which indicates a cough attack, in the analysis time interval. The predefined pressure threshold value for determining the cough events is preferably selected in a range of 30 hPa±3 hPa for adults, adolescents or children, or in a range of 20 hPa±1 hPa for infants and/or toddlers. The control unit preferably uses a time range of 20 sec to 60 sec or a number of 2 to 6 consecutive breathing cycles as an analysis time interval.

In another preferred embodiment, the control unit is configured to use a predefined minimum number of cough events, for example, an exceeding of a number of at least 2 to 6 cough events, on the basis of elevations of the flow rates $\dot{V}_{Pat}$ exhaled by the patient above the predefined flow rate threshold value as at least one evaluation criterion for analysis whether a state is present, which indicates a cough attack, in the analysis time interval. The predefined flow rate threshold value for determining the cough events is in this case selected by the control unit in a preferable range of 90 L/min to 180 L/min. The control unit preferably uses a time range of 20 sec to 60 sec or a range of 2 to 6 consecutive breathing cycles as the analysis time interval.

In a preferred embodiment, the control unit is configured to use a summary effect of individual cough events, i.e., events with corresponding elevations of the airway pressure $P_{AW}$ above the predefined pressure threshold value, by means of a formation of a time integral of the elevations of the airway pressure $P_{AW}$ in the analysis time interval, as at least one evaluation criterion for analysis whether a state is present, which indicates a cough attack. In this case, an exceeding of a predefined effect threshold value due to the cough events is assessed by the control unit as an indicator of the state of a cough attack assessed by the control unit. This predefined effect threshold value may be used in this case, for example, in units of pressure (hPa, mbar) or as a dimensionless numerical value. For this, a multiple of, e.g. 3 times to 5 times, the pressure threshold value is preferably selected. The control unit preferably uses a time range of 20 sec to 60 sec or a number of 2 to 6 breathing cycles as the analysis time interval.

In a preferred embodiment, the control unit is configured to use a volume exceeding a volume threshold value or a minimum quantity of a flow rate in the analysis time interval, corresponding to a minimum volume, which flows from the patient due to cough events in the analysis time interval, as at least one evaluation criterion for analysis whether a state is present, which indicates a cough attack. The predefined minimum volume may be selected in relation to the tidal volume $V_T$ or the minimum volume MV of the patient, for example, an integral volume of 10%-20% above the tidal volume or a sudden exceeding of the previously balanced minute volume by 5% to 10% may be selected as the volume threshold value. The exceeding of the predefined minimum volume may also be determined by means of an exceeding of a predefined volume threshold value as a volume value, which corresponds, for example, at least to 3 times to 5 times a typical tidal volume. With a typical tidal volume of 0.5 L+0.2 L, possible values of about 1 L to 3 L then arise for the minimum volume as well as for the volume threshold value.

In another preferred embodiment, the control unit is configured to use a summary effect of individual cough events, i.e., events with corresponding elevations of the flow rates $\dot{V}_{Pat}$ exhaled by the patient above the predefined flow rate threshold value, by means of a formation of a time integral of the elevations of the flow rates $\dot{V}_{Pat}$ exhaled by the patient in the analysis time interval, as at least one evaluation criterion for analysis whether a state is present, which indicates a cough attack. In this case, an exceeding of a predefined volume threshold value due to the cough events is assessed by the control unit as an indicator of the state of a cough attack. The predefined flow rate threshold value for determining the cough events is selected here by the control unit in a preferable range of 90 L/min to 180 L/min. The predefined volume threshold value is preferably selected by the control unit in relation to a typical tidal volume. With a typical tidal volume of 0.5 L±0.2 L, possible values of about 1 L to 3 L then arise for the volume threshold value. The control unit preferably uses a time range of 20 sec to 60 sec or a number of 2 to 6 consecutive breathing cycles as the analysis time interval.

In a preferred embodiment, the control unit is configured to use a summary effect of individual cough events, i.e., events with corresponding elevations of the airway pressure $P_{AW}$ above a predefined pressure threshold value, by means of a formation of a time integral of the elevations of the flow rates corresponding to the cough events in the analysis time interval, as at least one evaluation criterion for analysis whether a state is present, which indicates a cough attack. The predefined pressure threshold value for determining the cough events is preferably selected here in a range of 30 hPa+3 hPa for adults, adolescents or children, or in a range of 20 hPa+1 hPa for infants and/or toddlers. The predefined volume threshold value is also selected by the control unit in relation to the tidal volume. With a typical tidal volume of 0.5 L+0.2 L, possible values of about 1 L to 3 L then arise for the volume threshold value. The control unit preferably uses a time range of 20 sec to 60 sec or a number of 2 to 6 consecutive breathing cycles as the analysis time interval.

In a preferred embodiment, the control signal is transmitted from the alarm generation unit provided by the control unit to the output unit. The output unit is configured, preferably as part of the ventilator, to transmit the control signal, which indicates the state of cough attacks during the operation of the ventilator, directly or by means of an interface (WLAN, LAN, RS232, data bus, IrDA) into a system of devices in a data network (intranet, internet, PAN, WAN) and/or to an analysis unit (monitoring station, patient data management system).

In a preferred embodiment, the alarm generation unit is configured to output a message or a warning and/or generate a visual and/or acoustic warning or alarm, indicating the state, which indicates one or more cough attacks. Acoustic alarms may be outputted here, for example, by means of a sound-emitting component (loudspeaker, horn, speech output).

Visual alarms may be outputted by the alarm generation unit, for example, by means of a display screen (screen, touchscreen, tablet PC, smartphone), an illuminant (LED, LED), and also in text form (LCD row, LED row, dot matrix display).

The uses of the evaluation criteria according to the list (a.-e.) of evaluation criteria in the above-described embodiments of the method for operating a ventilator and of the ventilator with a determination of cough attacks using the evaluation criteria according to the list (a.-e.) of evaluation criteria represent solutions according to the present invention in themselves and in various combinations with one another in terms of the configuration of the analysis time intervals and of the predefined threshold values of pressure, flow rates, numbers of cough events, volumes, minimum volumes, time integrals of pressure and/or flow rates, wherein adaptations in the selected and/or used ranges of the threshold values and of the analysis time interval in case of combinations of these embodiments are likewise covered by the idea of the present invention.

The present invention is now explained in more detail by means of the following figures and the corresponding figure descriptions without limitations of the general idea of the present invention.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
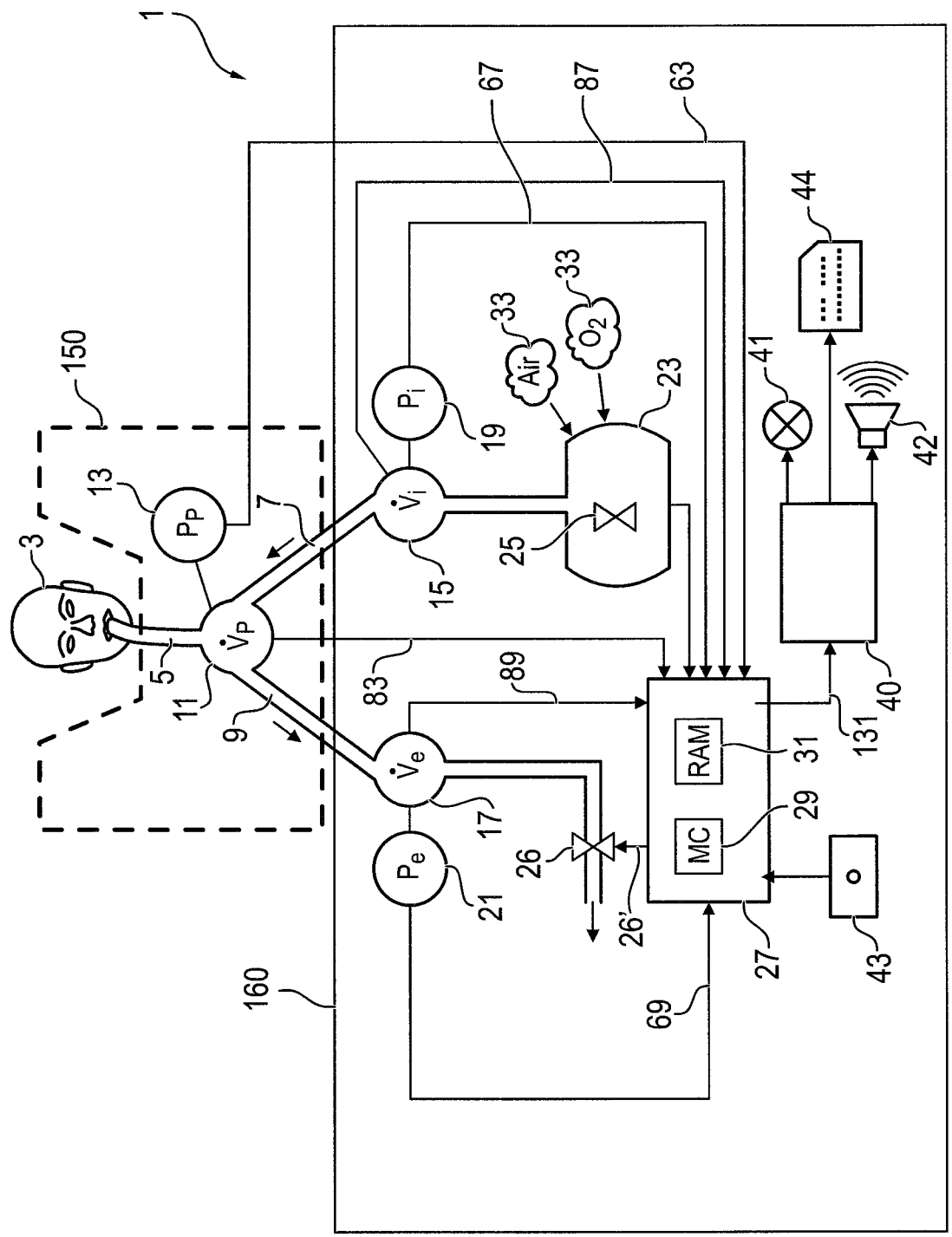
FIG. 1 is a schematic view of a ventilator configured suitably for mechanical ventilation.

Referring to the drawings, FIG. 1 shows a schematic view of a ventilator configured suitably for mechanical ventilation in the form of a ventilator 1 with its essential components.

The ventilator 1 has a control unit 27, which is preferably configured as an electronic control unit, which is configured suitably and intended for controlling or regulating a gas-mixing and -dispensing unit 23 with a dispensing valve device 25 arranged therein. Furthermore, measuring sites 15, 17, 19, 21 inside the ventilator 1 are shown in the ventilator 1. A measuring site for the inspiratory flow rate 15 and a measuring site for an inspiratory pressure 19 are arranged downstream of the gas-mixing and -dispensing unit 23. An inspiratory branch 7 of a patient gas supply line 5, via which the ventilator 1 supplies breathing gas via inhalation to the patient 3, is arranged following these measuring sites 15, 19. A measuring site for a patient flow rate 11 and for a patient pressure 13, starting from which the patient 3 is connected to the ventilator 1 via a patient gas supply line 5 usually configured as an endotracheal tube for exchanging inhaled and exhaled air, are connected to a so-called Y-piece directly at the patient 3, outside 150 the ventilator 1, but cooperating with the ventilator 1. As an alternative to the endotracheal tube, it is also possible to use non-invasive components for the patient gas supply as a patient gas supply line 5, such as masks, for example, nasal masks at the Y-piece. The air exhaled by the patient 3 is returned during exhalation to the ventilator 1 from the Y-piece at the patient 3 via an expiratory branch 9 of the patient gas supply line 5.

To control the ventilator 1 for the purpose of controlling the ventilation (breathing cycle, respiration rate, expiratory ventilation pressure), the pressure in the expiratory branch 9 and hence also the pressure present in the lungs of the patient 3 are set by means of an actuating signal 26' by the control unit 27 by means of an expiratory valve 26, often also called "PEEP" valve.

In addition, the control of the ventilation with cyclical alternation of inspiratory phases (inhalation) and expiratory phases (exhalation) (breathing cycle, respiration rate) is brought about via the expiratory valve 26 in conjunction with the control unit 27 and with the gas-mixing and -dispensing unit 23 with the dispensing valve device 25 arranged therein. A measuring site for the expiratory flow rate 17 and a measuring site for an expiratory pressure 21 are arranged inside or in the interior 160 of the ventilator 1 downstream of the expiratory branch 9 of the patient gas supply line 5. In alternative and special embodiments of ventilators 1, which are specially adapted to the application, such as emergency respirators or home ventilators as well as anesthesia apparatuses that also have components for ventilation in addition to the components necessary for anesthesia, measuring sites and components (sensors) may be distributed in relation to the components in the interior 160 and outside 150 differently from the embodiment shown in a simplified manner in this FIG. 1. For example, the components 15, 17, 19, 21 may thus be arranged outside 150 as well as inside 160 the ventilator. Such embodiments are also covered by the idea of the present invention, but they are not shown for reasons of a simplified view and for reasons of clarity. The exhaled air of the patient 3 is removed from these measuring sites 17, 21 to the surrounding area. The measuring sites 11, 13, 15, 17, 19, 21 and the flow sensor, or flow rate sensor and pressure sensor, which are arranged at these measuring sites, but are not shown in detail in this FIG. 1 for reasons of clarity, are each connected to the control unit 27 via respective suitable signal and data lines 63, 67, 69, 83, 87, 89. A flow-measuring unit and a pressure-measuring unit, which are not shown in this FIG. 1 for reasons of clarity, are configured in this FIG. 1 as units integrated into the control unit 27.

In addition to the flow-measuring unit and the pressure-measuring unit, the control unit 27 has suitably configured data processing and conversion units (signal amplification, signal filtering, A/D conversion), which are not shown in this schematic view according to FIG. 1, as well as a processor unit 29 and a memory unit 31 in order to configure and carry out the process of ventilation by and with the ventilator 1. The control unit 27 further carries out the analysis of the values provided by the pressure and flow sensors for a determination of cough attacks in an analysis time interval. In this analysis, threshold values of pressures, airway pressure, flow rates and volumes and minimum numbers of pressure elevations, flow rate elevations, volume elevations are included by the control unit 27 in the analysis time interval. The control unit may use one or more breathing cycles 70 (FIG. 2), one or more inspiratory phases (inhalation) 72, 72', 72'', 72''' (FIG. 2) or one or more expiratory phases (exhalation) 74, 74', 74'' (FIG. 2) as the analysis time interval.

The gases 33 needed for the ventilation, such as oxygen and air, are supplied to the gas-mixing and -dispensing unit 23 by means of supply lines not shown in this FIG. 1 and converted there by the dispensing valve device 25 into a gas mixture, which is suitable for ventilating the patient 3.

An alarm generation unit 40 with an optical signal generation element 41 and with an acoustic signal generation unit 42 is connected to the control unit in a wireless or wired manner in order to signal alarm situations that may occur during the operation of the ventilator 1 to the user. The connection is brought about such that a control signal 131 is generated and provided by the control unit 27. The control signal 131 indicates whether a state with one or more cough attacks has been present or is present in the analysis time interval. Furthermore, an output unit 44 for an output in text form or graphic form is arranged at the alarm generation unit 40 in order to output notices, alarms and messages to the user, for example, a warning concerning the state with cough attacks during the operation of the ventilator. In addition, an input unit 43, via which the user can perform both settings, such as ventilation parameters, e.g., respiration rate, tidal volume, ventilation pressures ($P_{insp}$, PEEP) and alarm limits corresponding thereto, such as maximum allowable airway pressure ($P_{aw-high}$), volume limits ($MV_{Low}$) at the ventilator 1, and can also perform settings, which make possible an analysis specific to the application for identification of cough events, for example, the input of predefined values for a predefined minimum number of cough events, threshold values of airway pressures, flow rates and volumes, the duration of the analysis time interval, is connected to the control unit 27. Furthermore, the input unit 43 is used for acknowledging signaled alarm situations.

Figure 2:
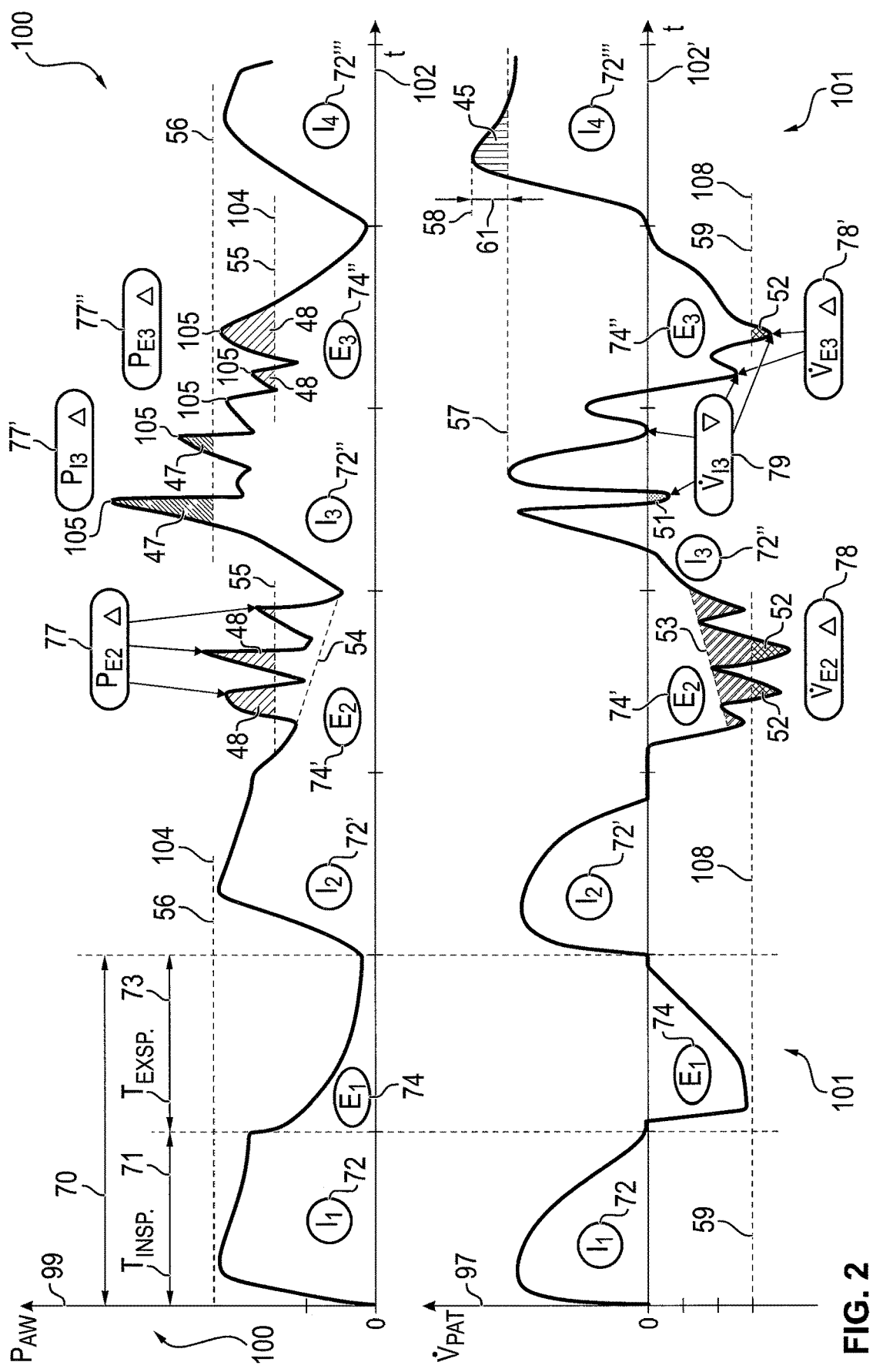
FIG. 2 is a set of signal-time diagrams with events clearly indicating cough attacks.

FIG. 2 shows signal curves for pressure, flow rate over time in the form of signal-time diagrams with events indicative of cough attacks.

FIG. 2 shows a pressure time curve 100 and a flow rate time curve 101. The pressure time curve 100 represents the curve of pressure measured values 99 (ordinate) with pressure threshold values 104 plotted over a time axis t (abscissa) 102. This pressure time curve 100 represents the airway pressure $P_{AW}$ on the ordinate. The airway pressure $P_{AW}$ is that pressure, which is set as a pressure for the patient 3 (FIG. 1) during inhalation and exhalation, caused by the ventilator, as well as due to his spontaneous breathing activity and can be measured there as airway pressure $P_{AW}$. The flow rate time curve 101 represents a curve of flow measured values V, 97 (ordinate) with flow threshold values 108, plotted over a time axis 102' (abscissa). The flow rate time curve 101 shows the patient flow rate $\dot{V}_{pat}$ with flow rates flowing into the patient 3 (FIG. 1), as well as flow rates flowing out of the patient 3 (FIG. 1). The flow rates flowing into the patient 3 (FIG. 1) are those flow rates above the abscissa 102' in the positive part of the ordinate 97, which are supplied by the ventilator to the patient 3 (FIG. 1) during inhalation (inspiration) or those provided to the patient 3 (FIG. 1) from the ventilator. The flow rates, which are shown below the abscissa 102' in the negative part of the ordinate 97, are the flow rates, which are exhaled away from the patient 3 (FIG. 1) in the direction of the surrounding area or in the direction of the ventilator in expiratory phases (exhalation) by the patient 3 (FIG. 1). The areas, which appear below the curves of the flow rate time curve 101, are respectively the volumes, which appear to be integral for the exhaled flow rates, or for the inhaled flow rates. A plurality of inspiratory phases (inhalation) and a plurality of respective following expiratory phases (exhalation) are shown in a cyclical course in the time curves 102, 102'. These inspiratory phases (inhalation) and exhalation with the corresponding pressure measured values $P_{AW}$ 99 and corresponding flow measured values $\dot{V}_{Pat}$ 97 are shown synchronized to one another in the time curves 102, 102' in this FIG. 2. A breathing cycle 70 not influenced by disturbances or coughs is shown in a first inspiratory phase (inhalation) 72 followed by a expiratory phase (exhalation) 74. This breathing cycle 70 shown and the other breathing cycles shown are distributed into a inspiratory phase (inhalation) 71 and a expiratory phase (exhalation) 73. The undisturbed breathing cycle 70 is followed by another inspiration 72', which follows another expiration 74', in which pressure elevations 77 arise. These pressure elevations arise, for example, in relation to a first upper pressure limit value 55 as well as in relation to a pressure comparison curve 54. This pressure comparison curve 54 quasi follows the curve of an undisturbed breathing cycle 70 with its decreasing pressure curve during the expiratory phase (exhalation) 74. Another inspiratory phase (inhalation) 72" follows the expiratory phase (exhalation) 74'. A pressure elevation 77' with a significant elevation 105 of the airway pressure $P_{AW}$ 99 above a second upper pressure limit value 56, as well as other elevations 77", 105 in the next expiratory phase (exhalation) 74" above a first upper pressure limit value 55 arise in this inspiratory phase (inhalation) 72". This inspiratory phase (inhalation) 72" passes over into a next expiratory phase (exhalation) 74", in which the elevations of the pressure 105 continue as exceedings of a first upper pressure limit value 55. The first upper pressure limit value 55 thus represents a pressure threshold value 104 for expiratory phases (exhalation), whereas the second upper pressure limit value 56 represents a pressure threshold value 104 for the inspiratory phases (inhalation). An analysis of the pressure time curve 100 with respect to the exceedings of the pressure threshold values 104 makes it possible to detect cough events. Thus, a cough event is clearly visible in the expiratory phase (exhalation) 74' in that the pressure threshold value 104, 55 was exceeded by three individual cough events, which form a shorter cough attack 77. In the next inhalation 72''' following the expiratory phase (exhalation) 74", it can be seen in the pressure signal curve 99 that the maximum value that is reached during the inhalation is reduced compared to the maximum value of the pressure that is reached in the undisturbed breathing cycle 70 in the inspiratory phase (inhalation) 72. This is explained by the fact that a volume deficit in the breathing circuit or even in the lungs of the patient 3 (FIG. 1) has developed due to the cough attacks, which deficit must be filled up again with a quantity of air through this inhalation 72m, wherein the pressure increase of the inhalation delays or even is absent with reduced amplitude. This can also be seen very well from the flow rate time curve 101. It can be seen there that a missing volume compensation arises in the inspiratory phase (inhalation) 72'. The flow rate time curve 101 is shown in FIG. 2 corresponding to the pressure time curve 100, wherein the events of pressure elevations 77, 77', 77" correspond to events of elevations of the patient flow rate 78, 78' as well as reductions of the patient flow rate 79. Lower flow limit values 59 and upper flow limit values 57, 58 can be applied as flow rate threshold values 108 to the flow measured values $\dot{V}_{Pat}$ 97 over the course of the flow rate time curve 101 for an analysis whether the determined pressure elevations 105 are corresponding to cough events 77, 77', 77". The inspiratory phases (inhalation) I1:72, I2:72', I3:72" and I4:72''', as well as the expiratory phases (exhalation) E1:74, E2:74' and E3:74" in the flow rate time curve 101 and the pressure time curve 100 are shown in FIG. 1 equally corresponding and synchronized over the course of time 102. A flow rate comparison curve 53 is illustrated in the flow rate time curve 101 in some sections in the expiratory phase (exhalation) E2:74', which can be used in the pressure time curve 100 in a similar manner as the pressure comparison curve 54 shown at E2:74' for distinguishing cough events as deviations from a normal breathing cycle 70, which is described by the inspiratory phase (inhalation) I1:72 and the expiratory phase (exhalation) E1:74. In addition to an exceeding or falling short of threshold values 108, 104, 55, 56, 57, 58, 59 or predefined courses of the curve 53, 54 by means of an amplitude comparison directly in the time curve 102, 102', it is also possible to determine areas under the time curves 101, 102 as integrals and to compare the areas with an area-specific threshold value in order to determine cough events and cough attacks as a summary quantity of individual cough events. The expiratory pressure integrals 48 in the pressure time curve 100 thus show a shorter cough attack 77. Individual, discrete pressure elevations 105, for example, in the inspiratory phase (inhalation) 72, 72', 72'', 72''' may also be used as an integral area of an inspiratory pressure integral 47 for a definition of a cough attack 77'. In a similar manner, an integral below the flow rate time curve 101 may also be formed in the flow rate time curve 101 based on the flow measured values $\dot{V}_{Pat}$ 97 in the signal course. For example, an expiratory flow rate integral 52 is shown in the expiratory elevation of the patient flow rate 78 in the expiratory phase (exhalation) 74'. This expiratory flow rate integral 52 corresponds, as it were, to an exhaled cough volume. The same applies to the flow rate integral 52 in the expiratory phase (exhalation) 74'' in the time curve 102'. An inspiratory flow rate integral 51 corresponding to the inspiratory reduction of the patient flow rate, which is shown as a flow rate, which flows away from the patient 3 (FIG. 1) as a volume during the duration of inhalation against the ventilation carried out by the ventilator 1 (FIG. 1), is shown as an example in the inhalation phase 72''. This flow rate flowing away from the patient 3 (FIG. 1) in the inhalation results in the inspiratory flow rate integral as a cough volume, which is due to a pressure elevation 105 in the inspiratory phase (inhalation) 72'' a pressure elevation 105 and is characteristic of a cough attack or a part of a cough attack. An inspiratory flow difference 61, which is clearly visible as an elevation compared to the first upper flow limit value 57, is shown in the flow rate time curve 101 in the inspiratory phase (inhalation) 72m. This elevation of the flow rate results in a missing volume compensation as a filling volume 45, which arises due to the fact that the patient 3 (FIG. 1) has exhaled more volume from his lungs during the previous expiratory phase (exhalation) 74'' than has been supplied in the previous breathing cycles of the lungs. An exceeding of the filling volume 45 by a predefined value or an exceeding of the inspiratory flow difference or of the missing volume flow compensation after a cough attack 77, 77', 77'' via a second upper flow limit value 58 can be assessed as an indicator of a previous cough attack 77, 77', 77''. These above-described methods of identifying clear signals as cough attacks and of characterizing a plurality of cough events or a certain cough volume as cough attacks in the flow rate time curve 101, as well as in the pressure time curve 100, as well as in combination of the two time curves 100, 101 are shown as examples and in an exemplary manner in time curves 102, 102' in this FIG. 2. The shown curve of pressure measured values 99 and flow measured values $\dot{V}_{Pat}$ 97 corresponds to only fictitious and analytically determined connections, which may be represented in a different manner when carrying out a real ventilation very essentially due to the selection of the ventilation parameters: respiration rate (RR), inspiration time to expiration time ratio (I:E ratio), positive end-expiratory pressure (PEEP), tidal volume ($V_T$) and other setting parameters for the fine adjustment of the ventilation. In this FIG. 2, the starting point is a pressure-controlled ventilation, similar situations with courses of the pressure time curve 100 and of the flow rate time curve 101 differing in some areas appear in a volume-controlled ventilation. Other influencing variables are given by other setting parameters such as triggering thresholds for detecting breathing activities when using modes of assisted ventilation.

While specific embodiments of the invention have been shown and described in detail to illustrate the application of the principles of the invention, it will be understood that the invention may be embodied otherwise without departing from such principles.

LIST OF REFERENCE DESIGNATIONS

1 Ventilator
3 Patient
5 Patient gas supply line
7 Inspiratory branch of the patient gas supply line
9 Expiratory branch of the patient gas supply line
11 Measuring site of the patient flow rate, Y-piece, connection element
13 Measuring site for patient pressure
15 Measuring site for inspiratory flow rate
17 Measuring site of expiratory flow rate
19 Inspiratory pressure, measuring site
21 Expiratory pressure, measuring site
23 Gas-mixing and -dispensing unit
25 Dispensing valve device
26 Expiratory valve
26' Actuating signal for the expiratory valve 26
27 Control unit, electronic control unit
29 Processor unit
31 Memory unit
40 Alarm generation unit, alarm output
41 Optical signal generation element
42 Acoustic signal generation element
43 Input unit
44 Output unit for text output, display screen
45 Filling volume
47 Inspiratory pressure integral
48 Expiratory pressure integral
51 Inspiratory flow rate integral
52 Expiratory flow rate integral
53 Flow rate comparison curve
54 Pressure comparison curve
55 First upper pressure limit value
56 Second upper pressure limit value
57 First upper flow limit value
58 Second upper flow limit value
59 Lower flow limit value
61 Inspiratory flow difference, missing volume compensation after cough attack
63, 67, 69 Signal/data lines of the pressure measuring sites
70 Breathing cycle
71 Inspiratory phase (inhalation) duration $T_{insp}$
72, 72', 72'', 72''' Time interval with inhalation (inspiration)
73 Expiratory phase (exhalation) duration $T_{exp}$
74, 74', 74'' Time interval with exhalation (expiration)
77, 77', 77'' Pressure elevations
78, 78' Expiratory elevations of the patient flow rate
79 Inspiratory reduction of the patient flow rate
83, 87, 89 Signal/data lines of the flow measuring sites 97 Flow-signal curve, flow measured values, (Y axis, ordinate)
99 Pressure signal curve, pressure measuring sites, (Y axis, ordinate)
100 Pressure-time curve
101 Flow rate-time curve
102, 102' Time axis t (X axis, abscissa)
104 Pressure threshold value
105 Elevations of the airway pressure ($P_{AW}$)
108 Flow rate threshold value
131 Control signal
150 Components arranged outside the device
160 Components arranged inside the device

What is claimed is:

1. A method for operating a ventilator with a determination of cough attacks, the method comprising the steps of:
providing a ventilator with a processor and sensors, the ventilator being configured for processing sensor signals of the ventilator provided by sensors, wherein the sensor signals indicate pneumatic/fluidic physical states of a breathing gas in a gas-carrying connection system which is connected and coupled in a gas-carrying manner to the ventilator and to a patient and is configured for transporting gases from and to the patient, from which values of an airway pressure prevailing in the gas-carrying connection system and of a flow rate, as well as of the flow directions corresponding to the flow rate in the gas-carrying connection system can be determined;
initializing an analysis time interval and a quantity of data;
detecting the pneumatic/fluidic physical states with determination of values of pressure and flow rates as the quantity of data;
determining whether an elevated situation of an interaction between the ventilator and the patient, with an elevated airway pressure, is present is based on a comparison to determine whether a comparison criterion indicating an elevated airway pressure is exceeded by the determined value of the airway pressure;
determining whether a quantity situation of an interaction between the ventilator and the patient is present, in which a smaller quantity of breathing gas is fed to the patient by the ventilator than flows from the patient is based on a comparison determining whether a comparison criterion indicating a flow rate in a corresponding flow direction is exceeded by the determined value of the flow rate in the corresponding flow direction;
determining whether a state, which indicates at least one cough attack, is present in the analysis time interval is based on at least one evaluation criterion, which includes one of the determined elevated situation and the quantity situation;
providing a control signal to an operator of the ventilator, which indicates a state, which indicates a cough attack;
updating of the analysis time interval and of the quantity of data,
the determination of the airway pressure being carried out based on values of at least one pressure sensor, of the sensors, for determination of the airway pressure; and
the at least one pressure sensor being arranged at a patient connection path or at a connection system and/or at an inspiratory connection system and/or at an expiratory connection system.

2. A method in accordance with claim 1, wherein:
a determination of the situation of the interaction between the ventilator and the patient, in which a smaller quantity of breathing gas is fed by the ventilator to the patient than flows from the patient, is carried out based on values of at least one flow sensor, of the sensors; and
the at least one flow sensor is arranged at a patient connection path or at a connection system and/or at an inspiratory connection system and/or at an expiratory connection system.

3. A method in accordance with claim 1, wherein a determination of the situation of the interaction between the ventilator and the patient, in which a smaller quantity of breathing gas is fed by the ventilator to the patient than flows from the patient, is based on information about the current breathing phase from a course of the control of the ventilator or is based on information about a state of an expiratory valve or an actuating signal for such an expiratory valve.

4. A method in accordance with claim 1, wherein a value of 20 sec to 40 sec is selected to be the analysis time interval or a value of 2 to 5 consecutive breathing cycles is selected to be the analysis time interval.

5. A method in accordance with claim 1, wherein a comparison with a predefined minimum number of cough events in the analysis time interval is used as at least one evaluation criterion for analysis whether the state is present, which indicates a cough attack.

6. A method in accordance with claim 1, wherein a comparison with a predefined minimum number of cough events based on elevations of the airway pressure above the predefined pressure threshold value is used as at least one evaluation criterion for analysis whether the state is present, which indicates a cough attack, in the analysis time interval.

7. A method in accordance with claim 1, wherein a comparison with a predefined minimum number of cough events based on elevations of the flow rates exhaled by the patient above the predefined flow rate threshold value is used as at least one evaluation criterion for analysis whether the state is present, which indicates a cough attack, in the analysis time interval.

8. A method in accordance with claim 1, wherein a summary effect of individual cough events, by means of formation of a time integral of elevations of airway pressure in the analysis time interval, is used as at least one evaluation criterion for analysis whether the state is present, which indicates a cough attack.

9. A method in accordance with claim 1, wherein a minimum quantity of a flow rate in the analysis time interval, corresponding to a minimum volume, which flows from the patient due to cough events in the analysis time interval, is used as at least one evaluation criterion for analysis whether the state is present, which indicates a cough attack.

10. A method in accordance with claim 1, wherein a summary effect of individual cough events, by means of formation of a time integral of elevations of flow rates exhaled by the patient in the analysis time interval, is used as at least one evaluation criterion for analysis whether the state is present, which indicates a cough attack.

11. A method in accordance with claim 1, wherein a summary effect of individual cough events, by means of formation of a time integral of flow rate elevations corresponding to the cough events in the analysis time interval, is used as at least one evaluation criterion for analysis whether the state is present, which indicates a cough attack.

12. A ventilator comprising:
a connection system configured for transporting breathing gases, the connection system comprising an expiratory path, configured and intended for carrying an expiratory quantity of breathing gas away from the patient, an inspiratory path configured and intended for carrying an inspiratory quantity of breathing gas from the ventilator to the patient, a patient connection path configured and intended for carrying the inspiratory quantity of breathing gas from the ventilator to the patient and for carrying the expiratory quantity of breathing gas away from the patient, wherein the expiratory path and the inspiratory path are connected to one another and to the patient connection path by means of a connection element;

a control unit;

a pressure-measuring unit comprising at least one pressure sensor arranged in or at the ventilator or the connection system and configured and intended for detecting a pressure measured value of a pressure that is prevailing in the connection system and wherein the pressure-measuring unit is configured for providing this at least one pressure measured value to the control unit as an airway pressure;

a flow-measuring unit comprising at least one flow sensor arranged in or at the connection system or in or at the ventilator and configured and intended for detecting at least one flow rate measured value of a quantity of breathing gas and a flow direction of the breathing gas corresponding to the flow rate measured value, which flows in the connection system from the patient or flows from the ventilator to the patient and wherein the flow-measuring unit is configured for providing this at least one flow rate measured value and the corresponding flow direction to the control unit; and an alarm generation unit, wherein the control unit is configured for effecting an initialization of an analysis time interval and of a quantity of data and for repeatedly carrying out the following sequence of steps after the initialization of an analysis time interval and of the quantity of data:

detecting of the pneumatic/fluidic physical states with determination of values of pressure and flow rates as a quantity of data;

determining whether an elevated situation of an interaction between the ventilator and the patient with an elevated airway pressure is present based on a comparison determining whether a comparison criterion indicating an elevated airway pressure is exceeded by the determined value of the airway pressure;

determining whether a quantity situation of an interaction between the ventilator and the patient is present, in which a smaller quantity of breathing gas is fed to the patient by the ventilator than flows from the patient based on a comparison determining whether a comparison criterion indicating a flow rate in a corresponding flow direction is exceeded by the determined value of the flow rate in the corresponding determined flow direction;

determining whether a state, which indicates at least one cough attack, is present in the analysis time interval based on at least one evaluation criterion, which includes one of the determined elevated situation and the quantity situation;

providing a control signal, which indicates a state, which indicates a cough attack; and updating of the analysis time interval and of the quantity of data.

13. A ventilator in accordance with claim 12, further comprising signal/data lines, wherein:

the at least one pressure sensor for detection of the pressure is arranged and configured at the patient connection path or at the connection element, and/or is arranged and configured at the inspiratory path, and/or is arranged and configured at the expiratory path; and the at least one pressure sensor is configured for transmitting signals of the pressure measured values to the control unit via the signal/data lines.

14. A ventilator in accordance with claim 12, further comprising signal/data lines, wherein:

the at least one flow sensor for detection of the flow rates is arranged and configured at the patient connection path or at the connection element, and/or is arranged and configured at the inspiratory path, and/or is arranged and configured at the expiratory path; and the at least one flow sensor is configured for transmitting signals of the flow rate measured values to the control unit via the signal/data lines.

15. A ventilator in accordance with claim 12, wherein the control unit is configured to determine whether the situation of an interaction between the ventilator and the patient is present, in which a smaller quantity of breathing gas is fed by the ventilator to the patient than flows from the patient, based on a difference from the signals of the flow sensor arranged in or at the expiratory path of the connection system and of the flow sensor arranged in or at the inspiratory path of the connection system.

16. A ventilator in accordance with claim 12, wherein the control unit, configured for determining the situation of the interaction between the ventilator and the patient, in which a smaller quantity of breathing gas is fed by the ventilator to the patient than flows from the patient, also takes into account information about a current breathing phase from a course of the control of the ventilator or information about a state of an expiratory valve or an actuating signal for such an expiratory valve.

17. A ventilator in accordance with claim 12, wherein a number of 2 to 5 consecutive breathing cycles or a value of 20 sec to 60 sec is used by the control unit as an analysis time interval.

18. A ventilator in accordance with claim 12, wherein a comparison with a predefined minimum number of cough events is used by the control unit as at least one evaluation criterion for analysis whether the state is present, which indicates a cough attack, in the analysis time interval.

19. A ventilator in accordance with claim 17, wherein a comparison with a predefined minimum number of cough events based on elevations of the airway pressure above the predefined pressure threshold value is used by the control unit as at least one evaluation criterion for analysis whether the state is present, which indicates a cough attack, in the analysis time interval.

20. A ventilator in accordance with claim 12, wherein a comparison with a predefined number of cough events based on elevations of the flow rates exhaled by the patient above the predefined flow rate threshold value is used by the control unit as at least one evaluation criterion for analysis whether the state is present, which indicates a cough attack, in the analysis time interval.

21. A ventilator in accordance with claim 12, wherein a summary effect of individual cough events, by means of formation of a time integral of the elevations of the airway pressure in the analysis time interval, is used by the control unit as at least one evaluation criterion for analysis whether the state is present, which indicates a cough attack.

22. A ventilator in accordance with claim 12, wherein a minimum quantity of a flow rate in the analysis time interval corresponding to a minimum volume, which flows from the patient due to cough events in the analysis time interval, is used by the control unit as at least one evaluation criterion for analysis whether the state is present, which indicates a cough attack.

23. A ventilator in accordance with claim 12, wherein a summary effect of individual cough events, by means of formation of a time integral of the elevations of the flow rates exhaled by the patient in the analysis time interval, is used by the control unit as at least one evaluation criterion for analysis whether the state is present, which indicates a cough attack.

24. A ventilator in accordance with claim 12, wherein a summary effect of individual cough events with corresponding elevations of the airway pressure, by means of formation of a time integral of the elevations of the airway pressures corresponding to the cough events in the analysis time interval, is used by the control unit as at least one evaluation criterion for analysis whether the state is present, which indicates a cough attack.

25. A ventilator in accordance with claim 12, wherein the control signal, which indicates the state of cough attacks during the operation of the ventilator, is transmitted by means of the alarm generation unit directly or by means of an interface in a system of devices in a data network and/or to an output unit.

26. A ventilator in accordance with claim 12, wherein the alarm generation unit is configured for outputting a message or a notice to the output unit and/or for triggering an alarm of the state, which indicates one or more cough attacks, by means of a visual and/or acoustic warning or alarm indicating the state.

27. A method for operating a ventilator with a determination of cough attacks of a patient, the method comprising the steps of:
  detecting the pneumatic/fluidic physical states with determination of values of pressure and flow rates as a quantity of data;
  determining whether an elevated airway pressure is present between the ventilator and the patient, based on a comparison to determine whether a comparison criterion indicating an elevated airway pressure is exceeded by the determined value of the airway pressure;
  determining whether a quantity situation is present between the ventilator and the patient in which a smaller quantity of breathing gas is fed to the patient by the ventilator than flows from the patient is based on a comparison determining whether a comparison criterion indicating a flow rate in a corresponding flow direction is exceeded by the determined value of the flow rate in the corresponding flow direction;
  determining whether a cough state, which indicates at least one cough attack, is present based on one of the determined elevated airway pressure and the quantity situation;
  providing a control signal to an operator of the ventilator which indicates whether the cough state is present.

* * * * *